United States Patent
Inoue et al.

(10) Patent No.: US 7,750,101 B2
(45) Date of Patent: Jul. 6, 2010

(54) POLYCYCLIC ESTER CONTAINING CYANO GROUP AND LACTONE SKELETON

(75) Inventors: Keizo Inoue, Himeji (JP); Takahiro Iwahama, Himeji (JP); Masamichi Nishimura, Himeji (JP); Kiyoharu Tsutsumi, Himeji (JP)

(73) Assignee: Daicel Chemical Industries, Ltd., Sakai-shi, Osaka (JP)

( * ) Notice: Subject to any disclaimer, the term of this patent is extended or adjusted under 35 U.S.C. 154(b) by 728 days.

(21) Appl. No.: 11/631,261

(22) PCT Filed: Sep. 26, 2006

(86) PCT No.: PCT/JP2006/319010
§ 371 (c)(1),
(2), (4) Date: Dec. 29, 2006

(87) PCT Pub. No.: WO2007/037213
PCT Pub. Date: Apr. 5, 2007

(65) Prior Publication Data
US 2008/0319160 A1    Dec. 25, 2008

(30) Foreign Application Priority Data
Sep. 28, 2005 (JP) .............................. 2005-282749

(51) Int. Cl.
*C08F 24/00* (2006.01)
*C07D 493/00* (2006.01)
(52) U.S. Cl. ................. 526/266; 526/268; 526/319; 526/320; 549/263
(58) Field of Classification Search ................. 526/266, 526/268, 319, 320; 549/263
See application file for complete search history.

(56) References Cited

U.S. PATENT DOCUMENTS

| | | | |
|---|---|---|---|
| 6,280,898 | B1 | 8/2001 | Hasegawa et al. |
| 6,451,788 | B1 | 9/2002 | Horrobin et al. |

FOREIGN PATENT DOCUMENTS

| | | | |
|---|---|---|---|
| JP | 2000-159758 | A | 6/2000 |
| JP | 2001-64273 | A | 3/2001 |
| JP | 2002-193961 | A | 7/2002 |
| JP | 2002-212174 | A | 7/2002 |
| JP | 2005-48126 | A | 2/2005 |
| JP | 2005-48128 | A | 2/2005 |
| JP | 2005-239828 | A | 9/2005 |

*Primary Examiner*—Helen L. Pezzuto
(74) *Attorney, Agent, or Firm*—Birch, Stewart, Kolasch & Birch, LLP

(57) ABSTRACT

Disclosed is a polycyclic ester containing a cyano group and a lactone skeleton, represented by following Formula (1):

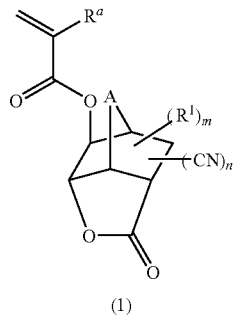

[Chemical Formula 1]

(1)

wherein $R^a$ represents, for example, a hydrogen atom or an alkyl group having one to six carbon atoms which may have a halogen atom; $R^1$s each represent, for example, a halogen atom or an alkyl or haloalkyl group having one to six carbon atoms; "m" is the number of $R^1$s; "n" is the number of cyano groups; and $CH_2=C(R^a)COO-$ group may have either of an endo conformation and an exo conformation. Accordingly, there is provided a novel polycyclic ester containing a cyano group and a lactone skeleton which is useful typically as a monomeric component for highly functional polymers. A polymer, for example, derived from this compound is highly soluble in an organic solvent while remaining stable typically to chemicals and exhibits improved hydrolyzability and/or improved solubility in water after hydrolysis.

2 Claims, No Drawings

POLYCYCLIC ESTER CONTAINING CYANO GROUP AND LACTONE SKELETON

TECHNICAL FIELD

The present invention relates to novel polycyclic esters each containing a cyano group and a lactone skeleton (6-oxabicyclo[3.2.1$^{1,5}$]octan-7-one derivatives and 3-oxatricyclo[4.2.1.0$^{4,8}$]nonan-2-one derivatives) and preparation processes thereof. Such polycyclic esters are useful typically as raw materials for coating compositions and functional polymers, and raw materials for fine chemicals such as medicaments and agricultural chemicals. It also relates to polycyclic alcohols each containing a cyano group and a lactone skeleton (4-hydroxy-6-oxabicyclo[3.2.1$^{1,5}$]octan-7-one derivatives and 5-hydroxy-3-oxatricyclo[4.2.1.0$^{4,8}$]nonan-2-one derivatives) and preparation processes thereof. Such polycyclic alcohols are useful as raw materials for the synthesis of the polycyclic esters. In addition, it relates to novel polymeric compounds containing monomeric units corresponding to the polycyclic esters each containing a cyano group and a lactone skeleton.

BACKGROUND ART

3-Oxatricyclo[4.2.1.0$^{4,8}$]nonan-2-one derivatives each having a polymerizable unsaturated group at the 5-position (i.e., 2-oxatricyclo[4.2.1.0$^{4,8}$]nonan-3-one derivatives each having a polymerizable unsaturated group at the 9-position) and 6-oxabicyclo[3.2.1$^{1,5}$]octan-7-one derivatives each having a polymerizable unsaturated group at the 4-position have a hydrophobic, bulky, and stable alicyclic carbocyclic ring and a hydrophilic and hydrolyzable lactone ring and contain a polymerizable unsaturated group. They are therefore used as, for example, raw materials for coating compositions and functional polymers using their specific structural properties. There have been proposed processes for easily and conveniently preparing these compounds (e.g., Patent Documents 1 and 2). The lactone rings of these compounds are hydrolyzable with bases, but the hydrolysis proceeds not so rapidly. The compounds may not sufficiently exhibit desired functions in some uses and/or their hydrolyzed products show low solubility in water and may thereby be poor in performance and be difficult to handle. They also have insufficient solubility in organic solvents.

Patent Document 1: Japanese Unexamined Patent Application Publication (JP-A) No. 2002-193961

Patent Document 2: Japanese Unexamined Patent Application Publication (JP-A) No. 2002-212174

DISCLOSURE OF INVENTION

Problems to be Solved by the Invention

Accordingly, an object of the present invention is to provide a novel polycyclic ester containing a cyano group and a lactone skeleton, and a process for efficiently preparing the same. A polymer, for example, derived from this compound may be highly soluble in an organic solvent while it remains stable and resistant to, for example, chemicals. The polycyclic ester can have improved hydrolyzability and/or improved solubility in water after hydrolysis and may be useful typically as a monomeric component for highly functional polymers.

Another object of the present invention is to provide a novel polycyclic alcohol containing a cyano group and a lactone skeleton, and a process for efficiently preparing the same. The polycyclic alcohol herein may be useful as a raw material for the synthesis of the polycyclic ester containing a cyano group and a lactone skeleton.

Yet another object of the present invention is to provide a novel polymeric compound which is highly stable and resistant to, for example, chemicals, is excellently soluble in an organic solvent, and is excellently hydrolyzable and/or a hydrolyzed product thereof is excellently soluble in water.

Means for Solving the Problems

After intensive investigations to achieve the objects, the present inventors have found a novel polycyclic ester containing a cyano group and a lactone skeleton and a process for efficiently preparing the polycyclic ester. A polymer, for example, derived from this compound is excellently soluble in an organic solvent. The lactone ring thereof is more hydrolyzable, and the resulting hydrolyzed product is more soluble in water than compounds in related art such as 3-oxatricyclo[4.2.1.0$^{4,8}$]nonan-2-one derivatives. In addition, the present inventors have found that a novel highly functional polymer is obtained from the polycyclic ester containing a cyano group and a lactone skeleton. The present invention has been achieved based on these findings.

Specifically, according to an embodiment of the present invention, there is provided a polycyclic ester containing a cyano group and a lactone skeleton, represented by following Formula (1):

[Chemical Formula 1]

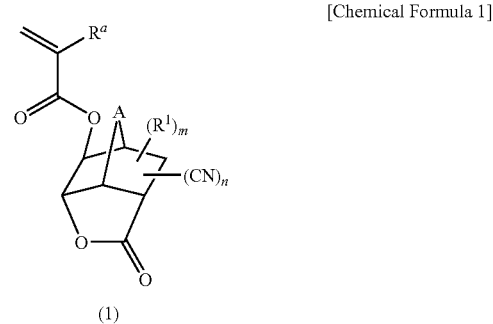

(1)

wherein $R^a$ represents a hydrogen atom, a halogen atom, or an alkyl group having one to six carbon atoms which may have a halogen atom; $R^1$s are substituents bound to a ring and each represent a halogen atom, an alkyl group having one to six carbon atoms which may have a halogen atom, a hydroxyalkyl group having one to six carbon atoms whose hydroxyl moiety may be protected by a protecting group and which may have a halogen atom, a carboxyl group which may form a salt, or a substituted oxycarbonyl group; "A" represents nonbonding or a methylene group; "m" is the number of $R^1$s and represents an integer of 0 to 8; "n" is the number of cyano groups (CN) bound to the ring and represents an integer of 1 to 9; and $CH_2$=$C(R^a)COO$— group may have either of an endo conformation and an exo conformation.

According to another embodiment of the present invention, there is provided a process for producing a polycyclic ester containing a cyano group and a lactone skeleton, the process including the step of reacting a polycyclic alcohol with an unsaturated carboxylic acid or a reactive derivative thereof to thereby yield a polycyclic ester, the polycyclic alcohol containing a cyano group and a lactone skeleton and being represented by following Formula (2):

[Chemical Formula 2]

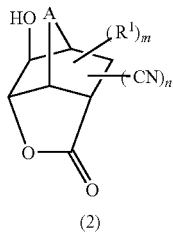

(2)

wherein $R^1$s are substituents bound to a ring and each represent a halogen atom, an alkyl group having one to six carbon atoms which may have a halogen atom, a hydroxyalkyl group having one to six carbon atoms whose hydroxyl moiety may be protected by a protecting group and which may have a halogen atom, a carboxyl group which may form a salt, or a substituted oxycarbonyl group; "A" represents nonbonding or a methylene group; "m" is the number of $R^1$s and represents an integer of 0 to 8; "n" is the number of cyano groups (CN) bound to the ring and represents an integer of 1 to 9; and "OH" may have either of an endo conformation and an exo conformation, the unsaturated carboxylic acid being represented by following Formula (3):

[Chemical Formula 3]

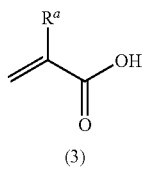

(3)

wherein $R^a$ represents a hydrogen atom, a halogen atom, or an alkyl group having one to six carbon atoms which may have a halogen atom, and the polycyclic ester being represented by following Formula (1):

[Chemical Formula 4]

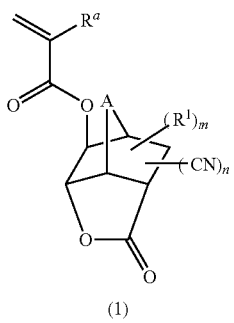

(1)

wherein $R^a$, $R^1$, "A", "m", and "n" are as defined above, and $CH_2$=$C(R^a)COO$— group may have either of an endo conformation and an exo conformation.

According to yet another embodiment of the present invention, there is provided a polycyclic alcohol containing a cyano group and a lactone skeleton, represented by following Formula (2):

[Chemical Formula 5]

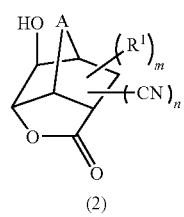

(2)

wherein $R^1$s are substituents bound to a ring and each represent a halogen atom, an alkyl group having one to six carbon atoms which may have a halogen atom, a hydroxyalkyl group having one to six carbon atoms whose hydroxyl moiety may be protected by a protecting group and which may have a halogen atom, a carboxyl group which may form a salt, or a substituted oxycarbonyl group; "A" represents nonbonding or a methylene group; "m" is the number of $R^1$s and represents an integer of 0 to 8; "n" is the number of cyano groups (CN) bound to the ring and represents an integer of 1 to 9; and "OH" may have either of an endo conformation and an exo conformation.

According to another embodiment of the present invention, there is provided a process for producing a polycyclic alcohol containing a cyano group and a lactone skeleton, the process including the step of subjecting an epoxy compound to a cyclization reaction to thereby yield a polycyclic alcohol, the epoxy compound being represented by following Formula (4):

[Chemical Formula 6]

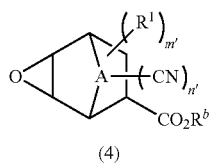

(4)

wherein $R^b$ represents an organic group; $R^1$s are substituents bound to a ring and each represent a halogen atom, an alkyl group having one to six carbon atoms which may have a halogen atom, a hydroxyalkyl group having one to six carbon atoms whose hydroxyl moiety may be protected by a protecting group and which may have a halogen atom, a carboxyl group which may form a salt, or a substituted oxycarbonyl group; "A" represents nonbonding or a methylene group; "m'" is the number of $R^1$s and represents an integer of 0 to 8; and "n'" is the number of cyano groups (CN) bound to the ring and represents an integer of 1 to 9, and the polycyclic alcohol being represented by following Formula (2):

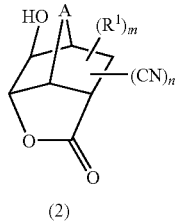

(2)

[Chemical Formula 7]

wherein $R^1$s are substituents bound to a ring and each represent a halogen atom, an alkyl group having one to six carbon atoms which may have a halogen atom, a hydroxyalkyl group having one to six carbon atoms whose hydroxyl moiety may be protected by a protecting group and which may have a halogen atom, a carboxyl group which may form a salt, or a substituted oxycarbonyl group; "A" represents nonbonding or a methylene group; "m" is the number of $R^1$s and represents an integer of 0 to 8; "n" is the number of cyano groups (CN) bound to the ring and represents an integer of 1 to 9; and "OH" may have either of an endo conformation and an exo conformation.

In addition, there is provided a polymeric compound including a monomeric unit represented by following Formula (I):

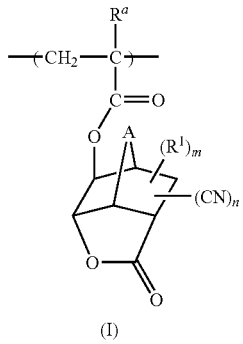

(I)

[Chemical Formula 8]

wherein $R^a$ represents a hydrogen atom, a halogen atom, or an alkyl group having one to six carbon atoms which may have a halogen atom; $R^1$s are substituents bound to a ring and each represent a halogen atom, an alkyl group having one to six carbon atoms which may have a halogen atom, a hydroxyalkyl group having one to six carbon atoms whose hydroxyl moiety may be protected by a protecting group and which may have a halogen atom, a carboxyl group which may form a salt, or a substituted oxycarbonyl group; "A" represents nonbonding or a methylene group; "m" is the number of $R^1$s and represents an integer of 0 to 8; and "n" is the number of cyano groups (CN) bound to the ring and represents an integer of 1 to 9; and —COO— group bound to a polymer chain may have either of an endo and an exo conformation.

The position numbers in 6-oxabicyclo[3.2.1$^{1,5}$]octane ring and those in 3-oxatricyclo[4.2.1.0$^{4,8}$]nonane ring are shown below at the left and the right, respectively.

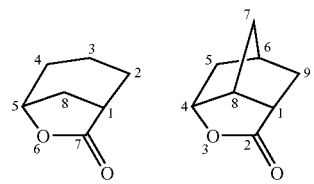

[Chemical Formula 9]

Advantages

According to the present invention, there are provided novel polycyclic esters containing a cyano group and a lactone skeleton, and process for efficiently preparing them. Polymers, for example, derived from the polycyclic esters are highly soluble in an organic solvent while they remain stable and resistant to, for example, chemicals. The polycyclic esters have improved hydrolyzability and/or solubility in water after hydrolysis and are useful typically as monomeric components for highly functional polymers. There are also provided novel polycyclic alcohols containing a cyano group and a lactone skeleton, and process for efficiently preparing them. The polycyclic alcohols herein are useful as a raw material for the synthesis of the polycyclic esters containing a cyano group and a lactone skeleton. In addition, there are also provided novel polymeric compounds which are highly stable and resistant to, for example, chemicals, are excellently soluble in an organic solvent, and are excellently hydrolyzable and/or hydrolyzed products thereof are excellently soluble in water.

BEST MODE FOR CARRYING OUT THE INVENTION

Polycyclic Ester Containing a Cyano Group and a Lactone Skeleton

Polycyclic esters containing a cyano group and a lactone skeleton (a 6-oxabicyclo[3.2.1$^{1,5}$]octan-7-one derivative and 3-oxatricyclo[4.2.1.0$^{4,8}$]nonan-2-one derivatives) according to an embodiment of the present invention are represented by Formula (1). In Formula (1), $R^a$ represents a hydrogen atom, a halogen atom, or an alkyl or haloalkyl group having one to six carbon atoms; $R^1$s are substituents bound to a ring [6-oxabicyclo[3.2.1$^{1,5}$]octane ring when "A" represents nonbonding, or 3-oxatricyclo[4.2.1.0$^{4,8}$]nonane ring when "A" is a methylene group] and each represent a halogen atom, an alkyl or haloalkyl group having one to six carbon atoms, a hydroxyalkyl or hydroxyhaloalkyl group having one to six carbon atoms whose hydroxyl moiety may be protected, a carboxyl group which may form a salt, or a substituted oxycarbonyl group; "A" represents nonbonding or a methylene group; "m" is the number of $R^1$s and represents an integer of 0 to 8; "n" is the number of cyano groups (CN) bound to the ring [6-oxabicyclo[3.2.1$^{1,5}$]octane ring when "A" represents nonbonding, or 3-oxatricyclo[4.2.1.0$^{4,8}$]nonane ring when "A" is a methylene group] and represents an integer of 1 to 9; and $CH_2$=C($R^a$)COO— group may have either of an endo conformation and an exo conformation.

The halogen atom includes, for example, fluorine, chlorine, and bromine atoms. Examples of the alkyl group having one to six carbon atoms include methyl, ethyl, propyl, isopropyl, butyl, isobutyl, s-butyl, t-butyl, pentyl, and hexyl groups. Among them, alkyl groups having one to four carbon atoms are preferred, of which methyl group is typically preferred. Examples of haloalkyl groups having one to six carbon atoms include chloroalkyl groups such as chloromethyl group; and fluoroalkyl groups such as trifluoromethyl, 2,2,2-trifluoroethyl, and pentafluoroethyl groups, of which fluoroalkyl groups having one to three carbon atoms are preferred.

The hydroxyalkyl group having one to six carbon atoms includes, for example, hydroxymethyl, 2-hydroxyethyl, 1-hydroxyethyl, 3-hydroxypropyl, 2-hydroxypropyl, 4-hydroxybutyl, and 6-hydroxyhexyl groups. Hydroxyhaloalkyl groups having one to six carbon atoms include, for example, difluorohydroxymethyl, 1,1-difluoro-2-hydroxyethyl, 2,2-difluoro-2-hydroxyethyl, and 1,1,2,2-tetrafluoro-2-hydroxyethyl groups. Of hydroxyalkyl or hydroxyhaloalkyl groups having one to six carbon atoms, hydroxyalkyl groups and hydroxyhaloalkyl groups each having one or two carbon atoms are preferred, of which those having one carbon atom are more preferred. Hydroxyl-protecting groups for hydroxyalkyl or hydroxyhaloalkyl groups having one to six carbon atoms may be protecting groups generally used as hydroxyl-protecting groups in organic syntheses. Specific examples thereof include methyl group, methoxymethyl group, and other groups which form an ether or acetal bond with oxygen atom constituting hydroxyl group; and acetyl group, benzoyl group, and other groups which form an ester bond with oxygen atom constituting hydroxyl group. Salts of carboxyl group include alkali metal salts, alkaline earth metal salts, and transition metal salts.

The substituted oxycarbonyl group includes, for example, alkoxycarbonyl groups such as methoxycarbonyl, ethoxycarbonyl, isopropyloxycarbonyl, and propoxycarbonyl groups, of which alkoxy-carbonyl groups whose alkoxy moieties each have one to four carbon atoms are preferred; alkenyloxycarbonyl groups such as vinyloxycarbonyl and allyloxycarbonyl groups, of which alkoxy-carbonyl groups whose alkoxy moieties each have two to four carbon atoms are preferred; cycloalkyloxycarbonyl groups such as cyclohexyloxycarbonyl group; and aryloxycarbonyl groups such as phenyloxycarbonyl group.

Preferred as $R^a$ are hydrogen atom; alkyl groups having one to three carbon atoms, such as methyl group; and haloalkyl groups having one to three carbon atoms, such as trifluoromethyl group, of which hydrogen atom or methyl group is typically preferred. Preferred as $R^1$ are alkyl groups and haloalkyl groups each having one to three carbon atoms, such as methyl group and trifluoromethyl group; hydroxyalkyl groups and hydroxyhaloalkyl groups each having one to three carbon atoms whose hydroxy moiety may be protected, of which hydroxymethyl groups which may be protected, such as hydroxymethyl group and acetoxymethyl group, are more preferred; and substituted oxycarbonyl groups.

The number "m" is 0 to 8, preferably 0 to 6, and more preferably 0 to 3. When there are plural $R^1$s, they may be the same as or different from each other. The number "n" is 1 to 9, preferably 1 to 5, and more preferably 1 or 2. When "A" represents nonbonding, cyano group(s) may be bound at any of the 1-, 2-, 3-, 4-, 5-, and 8-positions in 6-oxabicyclo[3.2.1$^{1,5}$]octane ring. Cyano group is preferably bound at the 1-position or 2-position, and is more preferably bound at the 1-position. When "A" is a methylene group, cyano group(s) may be bound at any of the 1-, 4-, 5-, 6-, 7-, 8-, and 9-positions in 3-oxatricyclo[4.2.1.0$^{4,8}$]nonane ring. Cyano group is preferably bound at the 1-position or the 9-position, and is more preferably bound at the 1-position.

Representative examples of polycyclic esters containing a cyano group and a lactone skeleton, represented by Formula (1) include 1-cyano-6-oxabicyclo[3.2.1$^{1,5}$]octan-7-one compounds including their stereoisomers, 2-cyano-6-oxabicyclo[3.2.1$^{1,5}$]octan-7-one compounds including their stereoisomers, 1-cyano-5-(meth)acryloyloxy-3-oxatricyclo[4.2.1.0$^{4,8}$]nonan-2-one compounds including their stereoisomers, and 9-cyano-5-(meth)acryloyloxy-3-oxatricyclo[4.2.1.0$^{4,8}$]nonan-2-one compounds including their stereoisomers. These compounds are represented by following formulae, in which R represents acryloyl group or methacryloyl group; and Ac represents acetyl group.

[Chemical Formula 10]

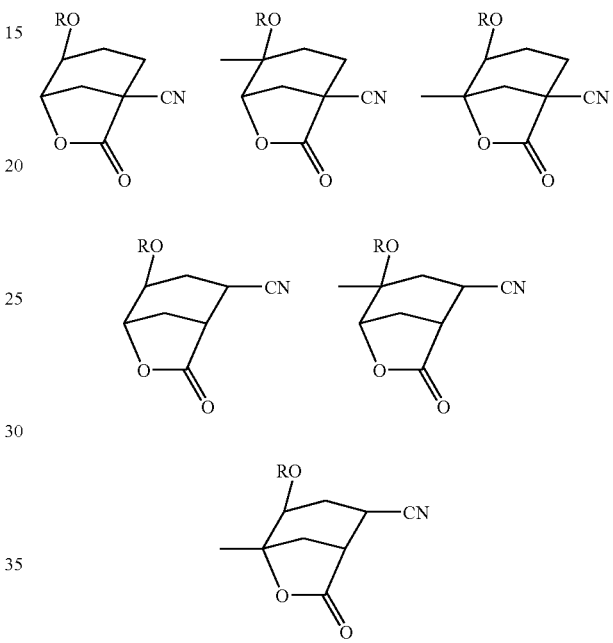

[Chemistry Formula 11]

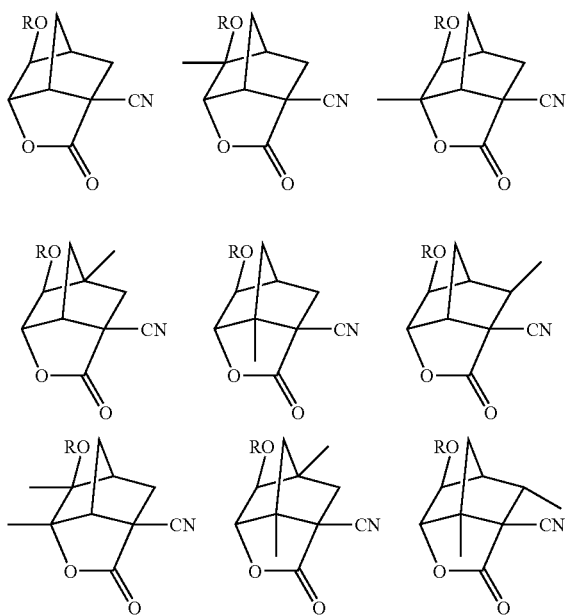

-continued

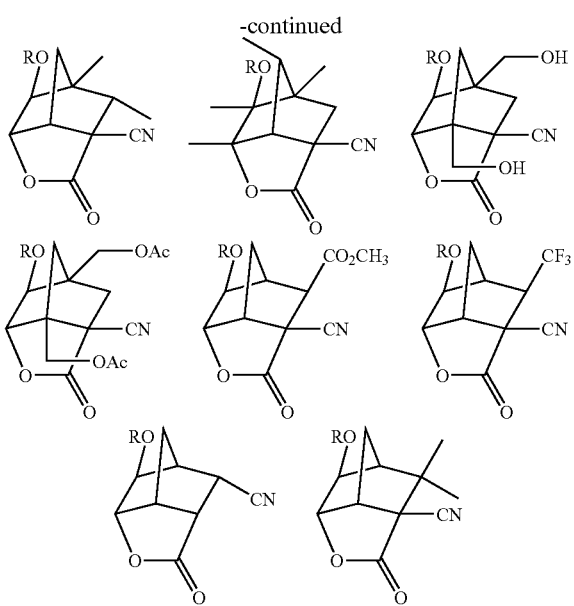

Polycyclic esters each containing a cyano group and a lactone skeleton, represented by Formula (1) may each be prepared by reacting a polycyclic alcohol containing a cyano group and a lactone skeleton and being represented by Formula (2) (a 4-hydroxy-6-oxabicyclo[3.2.1$^{1,5}$]octan-7-one derivative or a 5-hydroxy-3-oxatricyclo[4.2.1.0$^{4,8}$]nonan-2-one derivative) with an unsaturated carboxylic acid represented by Formula (3) or a reactive derivative thereof. Specific examples and preferred examples or preferred ranges of $R^a$, $R^1$, "m", and "n" in Formulae (2) and (3) are as above.

Representative examples of unsaturated carboxylic acids represented by Formula (3) include acrylic acid, methacrylic acid, and alpha-trifluoromethylacrylic acid. Reactive derivatives of unsaturated carboxylic acids represented by Formula (3) include acid halides, acid anhydrides, and esters. Representative examples of polycyclic alcohols each containing a cyano group and a lactone skeleton, represented by Formula (2) include compounds corresponding to, except with R being hydrogen atom, the compounds listed as the representative examples of polycyclic esters each containing a cyano group and a lactone skeleton, represented by Formula (1).

The polycyclic esters each containing a cyano group and a lactone skeleton, represented by Formula (1) may more specifically be prepared, for example, by process (a), (b), or (c). In the process (a), a compound represented by Formula (2) is reacted with an active, reactive derivative of an unsaturated carboxylic acid in a solvent where necessary in the presence of a base. The solvent herein includes tetrahydrofuran, toluene, and methylene chloride. The base includes triethylamine, pyridine, and 4-dimethylaminopyridine. The reactive derivative includes (meth)acryloyl halides such as (meth)acryloyl chlorides; and (meth)acrylic anhydrides. In the process (b), a compound represented by Formula (2) is reacted with an unsaturated carboxylic acid ester such as methyl (meth)acrylate in a solvent in the presence of a transesterification catalyst such as titanium isopropoxide. The solvent herein can be the same as above. In the process (c), a compound represented by Formula (2) is reacted with an unsaturated carboxylic acid, such as (meth)acrylic acid, in a solvent in the presence of a strong acid. The solvent herein can be the same as above. The strong acid includes hydrochloric acid, sulfuric acid, and p-toluenesulfonic acid.

Reaction conditions in these processes may be as in general processes for the preparation of esters. For example, in the process (a), the amount of an active/reactive derivative of unsaturated carboxylic acid is, for example, about 1 to about 1.5 moles to 1 mole of a compound represented by Formula (2), and the amount of a base is, for example, about 1 to about 3 moles to 1 mole of an active/reactive derivative of unsaturated carboxylic acid. The base may be used in large excess. A reaction temperature is, for example, about −20° C. to 50° C. In the process (b), the amount of an unsaturated carboxylic acid ester is, for example, about 1 to about 10 moles to 1 mole of a compound represented by Formula (2). The ester may be used in large excess. The amount of a transesterification catalyst is, for example, about 0.0001 to about 1 mole to 1 mole of a compound represented by Formula (2). A reaction temperature is, for example, about 0° C. to about 150° C. In the process (c), the amount of an unsaturated carboxylic acid is, for example, about 1 to about 5 moles to 1 mole of a compound represented by Formula (2). The unsaturated carboxylic acid may be used in large excess. The amount of a strong acid is, for example, about 0.0001 to about 1 mole to 1 mole of a compound represented by Formula (2). A reaction temperature is, for example, about 0° C. to about 150° C. In these reactions, a polymerization inhibitor such as hydroquinone monomethyl ether, or oxygen may be introduced in order to prevent polymerization.

Polycyclic esters each containing a cyano group and a lactone skeleton formed as a result of a reaction can be separated and purified, for example, by a separation procedure such as filtration, concentration or enrichment, distillation, extraction, crystallization, recrystallization, or column chromatography, or any combination of these procedures.

Polycyclic alcohols each containing a cyano group and a lactone skeleton and being represented by Formula (2) can each be prepared by subjecting an epoxy compound represented by Formula (4) (a cyclohexene oxide derivative or a 2,3-epoxybicyclo[2.2.1]heptane derivative) to a cyclization reaction. The substituent $R^1$ in Formula (4) is as defined above. The number "m'" represents 0 to 8, and is preferably 0 to 6, and more preferably 0 to 3. The number "n'" represents 1 to 9 and is preferably 1 to 5, and more preferably 1 or 2.

Organic groups as $R^b$ can be any organic groups capable of constituting a carboxylic acid ester and include, for example, alkyl groups such as methyl, ethyl, propyl, isopropyl, butyl, and t-butyl groups, of which alkyl groups each having one to six carbon atoms are preferred; alkenyl groups such as vinyl and allyl groups, of which alkenyl groups each having one to six carbon atoms are preferred; cycloalkenyl groups such as cyclohexyl group; aryl groups such as phenyl group; and heterocyclic groups such as pyridyl group. Among them, preferred as $R^b$ are hydrogen atom, as well as alkyl groups each having one to four carbon atoms, such as methyl and ethyl groups.

When $R^b$ is a hydrogen atom, a cyclization reaction proceeds simply by dissolving a compound represented by Formula (4) in a solvent. When $R^b$ is an organic group, a compound represented by Formula (4) is subjected to a conventional hydrolysis reaction to thereby form a corresponding compound in which $R^b$ is hydrogen atom, and a cyclization reaction proceeds immediately to thereby yield a compound represented by Formula (2). Such hydrolysis reactions include alkaline hydrolysis reactions, acid hydrolysis reactions, and neutral hydrolysis reactions. A polycyclic alcohol containing a cyano group and a lactone skeleton and being represented by Formula (2) is formed as a result of the reaction. It can be separated and purified, for example, by a separation procedure such as filtration, concentration or enrichment, distillation, extraction, crystallization, recrystallization, or column chromatography, or any combination of these procedures.

Of compounds represented by Formula (2), compounds each having one or more fluorine atoms bound to a ring can also be prepared by subjecting a compound having at least one hydrogen atom bound to a ring to a conventional fluorination reaction using a fluorinating agent such as fluorine.

Epoxy compounds represented by Formula (4) can be prepared, for example, according to the following reaction process formula. In the formula, $R^{1a}$s are substituents bound to a diene chain or cyclopentadiene ring and each represent a halogen atom, an alkyl or haloalkyl group having one to six carbon atoms, a hydroxyalkyl or hydroxyhaloalkyl group having one to six carbon atoms whose hydroxyl moiety may be protected, a carboxyl group which may form a salt, a substituted oxycarbonyl group, or a cyano group; $R^{1b}$s are substituents bound to a carbon atom constituting a carbon-carbon double bond and each represent a halogen atom, an alkyl or haloalkyl group having one to six carbon atoms, a hydroxyalkyl or hydroxyhaloalkyl group having one to six carbon atoms whose hydroxyl moiety may be protected, a carboxyl group which may form a salt, a substituted oxycarbonyl group, or a cyano group; "i" is the number of $R^{1a}$ and represents an integer of 0 to 6; "j" is the number of $R^{1b}$ and represents an integer of 0 to 3; at least one of $iR^{1a}$s and $jR^{1b}$s is a cyano group; "A" is as defined above; and definitions, specific examples, and preferred examples or preferred ranges of $R^1$, $R^b$, "m", and "n" are as above.

[Chemical Formula 12]

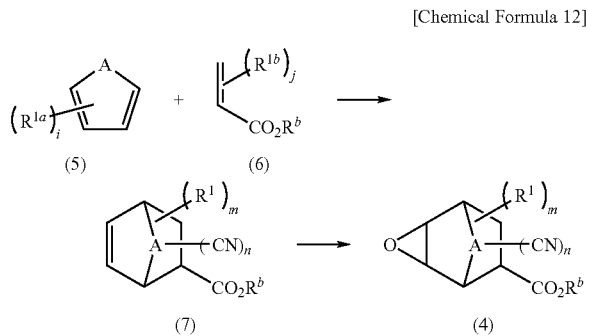

Specifically, epoxy compounds represented by Formula (4) (cyclohexene oxide derivatives and 2,3-epoxybicyclo[2.2.1]heptane derivatives) can each be obtained by subjecting a butadiene derivative or cyclopentadiene derivative represented by Formula (5), and an unsaturated carboxylic acid represented by Formula (6) or an ester thereof to a Diels-Alder reaction to thereby yield a cyclohexene derivative or bicyclo[2.2.1]hept-2-ene derivative represented by Formula (7), and reacting this with a peracid or peroxide. When $R^b$ is, for example, a hydrogen atom, a compound represented by Formula (2) may be obtained as a main product by reacting a compound represented by Formula (7) with a peracid or peroxide so as to induce cyclization immediately after epoxidation.

Representative examples of butadienes and cyclopentadiene derivatives represented by Formula (5) include butadiene, isoprene, 1,3-cyclopentadiene, 1-methyl-1,3-cyclopentadiene, 2-methyl-1,3-cyclopentadiene, 5-methyl-1,3-cyclopentadiene, 1,2-dimethyl-1,3-cyclopentadiene, 1,4-dimethyl-1,3-cyclopentadiene, 2,3-dimethyl-1,3-cyclopentadiene, 1,2,3,4-tetramethyl-1,3-cyclopentadiene, 1,2,3,4,5-pentamethyl-1,3-cyclopentadiene, 1-hydroxymethyl-1,3-pentadiene, 1,4-bis(hydroxymethyl)-1,3-cyclopentadiene, 2,3-bis(hydroxymethyl)-1,3-cyclopentadiene, 1-acetoxymethyl-1,3-cyclopentadiene, 1,4-bis(acetoxymethyl)-1,3-cyclopentadiene, and 2,3-bis(acetoxymethyl)-1,3-cyclopentadiene.

A reaction between a compound represented by Formula (5) and a compound represented by Formula (6) may be carried out in the presence of, or in the absence of, a solvent. The solvent includes, for example, esters such as ethyl acetate; organic acids such as acetic acid; alcohols such as t-butyl alcohol; halogenated hydrocarbons such as chloroform, dichloromethane, and 1,2-dichloroethane; aromatic hydrocarbons such as benzene and toluene; aliphatic hydrocarbons such as hexane, heptane, and octane; alicyclic hydrocarbons such as cyclohexane; amides such as N,N-dimethylformamide, and N,N-dimethylacetamide; nitriles such as acetonitrile, propionitrile, and benzonitrile; and chain or cyclic ethers such as ethyl ether and tetrahydrofuran. Each of these solvents can be used alone or in combination.

A system may further include a Lewis acid in order to improve a reaction rate and reaction selectivities such as stereoselectivity. Such Lewis acids include, but are not limited to, $AlCl_3$, $SnCl_4$, $TiCl_4$, $BF_3$, and $ZnI_2$. A reaction temperature can be appropriately set according typically to the types of reaction materials and is generally about −80° C. to about 300° C., and preferably about −70° C. to about 250° C. A reaction may be carried out under ordinary pressure or under a pressure (under a load). A reaction may be conducted according to any system such as a batch system, a semi-batch system, or a continuous system. The resulting compounds represented by Formula (7) can be separated and purified, for example, by a separation procedure such as filtration, concentration or enrichment, distillation, extraction, crystallization, recrystallization, or column chromatography, or any combination of these procedures.

Of peracids and peroxides to be reacted with a compound represented by Formula (7), peracids include organic peracids such as performic acid, peracetic acid, trifluoroperacetic acid, perbenzoic acid, m-chloroperbenzoic acid, and monoperoxyphthalic acid; and inorganic peracids such as permanganic acid. Organic peracids can be equilibrium peracids such as equilibrium performic acid and equilibrium peracetic acid. Specifically, it is acceptable that an organic acid such as formic acid or acetic acid is used in combination with hydrogen peroxide to thereby yield a corresponding organic peracid in the system. When an equilibrium peracid is used, a small amount of a strong acid, such as sulfuric acid, can be used as a catalyst. The amount of a peracid is, for example, about 0.8 to about 2 moles, preferably about 0.9 to about 1.5 moles, and more preferably about 0.95 to about 1.2 moles, to 1 mole of the compound represented by Formula (7).

Peroxides to be reacted with a compound represented by Formula (7) include hydrogen peroxide, peroxides, hydroperoxides, peroxoacids, and salts of peroxoacids. Hydrogen peroxide for use herein can be pure hydrogen peroxide, but it may be a hydrogen peroxide diluted with a suitable solvent such as water, from the viewpoint of handleability. For example, it may be used as a 30 percent by weight aqueous solution of hydrogen peroxide. The amount of a peroxide such as hydrogen peroxide is, for example, about 0.9 to about 5 moles, preferably about 0.9 to about 3 moles, and more preferably about 0.95 to about 2 moles, to 1 mole of the compound represented by Formula (7).

The hydrogen peroxide is often used in combination with a metal compound. Such metal compounds include, for example, oxides, oxoacids or salts thereof, sulfides, halides, oxyhalides, borides, carbides, silicides, nitrides, phosphides, peroxides, complexes including inorganic complexes and organic complexes, and organic metal compounds, each containing one or more metal elements such as tungsten (W), molybdenum (Mo), vanadium (V), manganese (Mn), and rhenium (Re). Each of these metal compounds can be used alone or in combination.

The oxides include, for example, tungsten oxides such as $WO_2$ and $WO_3$; molybdenum oxides such as $MoO_2$ and $MoO_3$; vanadium oxides such as $VO$, $V_2O_3$, $VO_2$, and $V_2O_5$; manganese oxides such as $MnO$, $Mn_2O_3$, $Mn_3O_4$, $MnO_2$, and $Mn_2O_7$; and multicomponent oxides containing metal elements such as W, Mo, V, and Mn.

The oxoacids include, for example, tungstic acid, molybdic acid, vanadic acid, and manganic acid; isopolyacids such as isopolytungstic acid, isopolymolybdic acid, and isopolyvanadic acid; and heteropolyacids each containing the metal element in combination typically with another metal element, such as phosphotungstic acid, silicotungstic acid, phosphomolybdic acid, silicomolybdic acid, and phosphovanadomolybdic acid. The other metal element in such heteropolyacids is preferably phosphorus or silicon, of which phosphorus is more preferred.

Salts of oxoacids include, of the above-mentioned oxoacids, alkali metal salts such as sodium salts and potassium salts; alkaline earth metal salts such as magnesium salts, calcium salts, and barium salts; ammonium salts; and transition metal salts. Salts of oxoacids such as salts of heteropolyacids may be corresponding salts, in which part of hydrogen atoms serving as a cation are replaced with another cation.

Peroxides containing metal elements include, for example, peroxoacids such as peroxotungstic acid, peroxomolybdic acid, and peroxovanadic acid; salts of peroxoacids, such as alkali metal salts, alkaline earth metal salts, ammonium salts, and transition metal salts of the peroxoacids; peracids such as permanganic acid; and salts of peracids, such as alkali metal salts, alkaline earth metal salts, ammonium salts, and transition metal salts of the peracids.

The amount of a metal compound to be used with the hydrogen peroxide is, for example, about 0.0001 to about 2 moles, preferably about 0.0005 to about 0.5 moles, and more preferably about 0.001 to about 0.2 moles, to 1 mole of a compound represented by Formula (7).

A reaction between a compound represented by Formula (7) and a peracid or peroxide may be carried out in the presence of, or in the absence of, a solvent. Examples of the solvent include alcohols such as t-butyl alcohol; halogenated hydrocarbons such as chloroform, dichloromethane, and 1,2-dichloroethane; aromatic hydrocarbons such as benzene; aliphatic hydrocarbons such as hexane, heptane, and octane; alicyclic hydrocarbons such as cyclohexane; amides such as N,N-dimethylformamide and N,N-dimethylacetamide; nitrites such as acetonitrile, propionitrile, and benzonitrile; chain or cyclic ethers such as ethyl ether and tetrahydrofuran; esters such as ethyl acetate; organic acids such as acetic acid; and water. Each of these solvents can be used alone or in combination. When the reaction is carried out in a heterogenous system, water or an aqueous (water-containing) solvent is often used.

A reaction temperature can be set appropriately in consideration of the rate and selectivity of the reaction, and is generally about −10° C. to about 100° C., and preferably about 0° C. to about 80° C. The reaction may be carried out according to any system such as a batch system, a semi-batch system, or a continuous system.

The reaction induces epoxidation of a double bond in the compound represented by Formula (7) to thereby yield an epoxy compound represented by Formula (4). When $R^b$ is hydrogen atom, for example, an intramolecular cyclization reaction accompanied with ring-opening of an epoxy ring may proceed and there may be formed a polycyclic alcohol containing a cyano group and a lactone skeleton represented by Formula (2).

An epoxy compound represented by Formula (4) and a compound represented by Formula (2) formed as a result of reaction can be separated and purified, for example, by a separation procedure such as filtration, concentration or enrichment, distillation, extraction, crystallization, recrystallization, or column chromatography, or any combination of these procedures.

A compound represented by (1) having one or more fluorine atoms bound to the ring shown in Formula (1) can also be prepared by subjecting a compound represented by Formula (1) having one or more hydrogen atom bound to the ring shown in Formula (1) to a conventional fluorination reaction using a fluorinating agent such as fluorine.

Polycyclic esters containing a cyano group and a lactone skeleton according to the present invention can be used typically as raw materials for coating compositions and functional polymers, and raw materials for fine chemicals such as medicaments and agricultural chemicals.

[Polymeric Compound]

A polymeric compound according to the present invention contains a monomeric unit (constitutional repeating unit) corresponding to a polycyclic ester containing a cyano group and a lactone skeleton and being represented by Formula (1). In other words, it contains a monomeric unit represented by Formula (I). The polymeric compound may contain one or more different monomeric units represented by Formula (I). Such a polymeric compound can be prepared by subjecting a polycyclic ester containing a cyano group and a lactone skeleton and being represented by Formula (1) to polymerization.

Monomeric units represented by Formula (1) each have a 6-oxabicyclo[$3.2.1^{1,5}$]octan-7-one skeleton having a cyano group, or a 3-oxatricyclo[$4.2.1.0^{4,8}$]nonan-2-one skeleton having a cyano group. In these monomeric units, a lactone ring constituting part of the 6-oxabicyclo[$3.2.1^{1,5}$]octan-7-one skeleton or the 3-oxatricyclo[$4.2.1.0^{4,8}$]nonan-2-one skeleton is more susceptible to hydrolysis, and hydrolyzed polymers are more soluble in water than in monomeric units containing a 6-oxabicyclo[$3.2.1^{1,5}$]octan-7-one skeleton having no cyano group, or a 3-oxatricyclo[$4.2.1.0^{4,8}$]nonan-2-one skeleton having no cyano group. Accordingly, polymeric compounds according to the present invention are useful as highly functional polymers for use in fields in which polymers are desirably capable of acquiring water-solubility as a result of a predetermined treatment.

Polymeric compounds according to the present invention may each contain one or more other monomeric units in accordance with the application and required functions thereof, in addition to a monomeric unit represented by Formula (I). Such another monomeric unit can be formed by carrying out copolymerization of a polymerizable unsaturated monomer corresponding to the other monomeric unit with a polycyclic ester containing a cyano group and a lactone skeleton, represented by Formula (1).

Polymerizable unsaturated monomers corresponding to the other monomeric units include, for example, monomers that can form carboxyl group as a result typically of a decomposition reaction. Examples of such monomers are compounds represented by following Formulae (8a), (8b), (8c), and (8d).

[Chemical Formula 13]

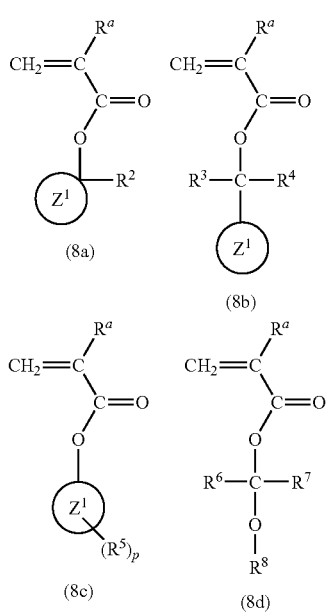

In these formulae, Ring $Z^1$ represents a substituted or unsubstituted alicyclic hydrocarbon ring having six to twenty carbon atoms; $R^a$ is as defined above; $R^2$, $R^3$, and $R^4$ are the same as or different from one another and each represent a substituted or unsubstituted alkyl group having one to six carbon atoms; $R^5$s are substituents bound to Ring $Z^1$, are the same as or different from one another and each represent an oxo group, an alkyl group, a protected or unprotected hydroxyl group, a protected or unprotected hydroxyalkyl group, or a protected or unprotected carboxyl group, where at least one of $pR^5$s represents a —$COOR^c$ group, wherein $R^c$ represents a substituted or unsubstituted tertiary hydrocarbon group, a tetrahydrofuranyl group, a tetrahydropyranyl group, or an oxepanyl group; "p" represents an integer of 1 to 3; $R^6$ and $R^7$ are the same as or different from each other and represent a hydrogen atom or a substituted or unsubstituted alkyl group having one to six carbon atoms; and $R^8$ represents a hydrogen atom or an organic group, in which at least two of $R^6$, $R^7$, and $R^8$ may be combined to form a ring with an adjacent atom.

In Formulae (8a), (8b), and (8c), the alicyclic hydrocarbon ring having six to twenty carbon atoms in Ring $Z^1$ can be a monocyclic ring or a polycyclic ring such as a fused ring or bridged ring. Representative examples of alicyclic hydrocarbon rings include cyclohexane ring, cyclooctane ring, cyclodecane ring, adamantane ring, norbornane ring, norbornene ring, bornane ring, isobornane ring, perhydroindene ring, decalin ring, perhydrofluorene ring (tricyclo[7.4.0.0$^{3,8}$]tridecane ring), perhydroanthracene ring, tricyclo[5.2.1.0$^{2,6}$]decane ring, tricyclo[4.2.2.1$^{2,5}$]undecane ring, and tetracyclo[4.4.0.1$^{2,5}$.1$^{7,10}$]dodecane ring. The alicyclic hydrocarbon ring may be substituted. Substituents herein include alkyl groups such as methyl group, of which alkyl groups having one to four carbon atoms are preferred; halogen atoms such as chlorine atom; protected or unprotected hydroxyl groups; oxo group; and protected or unprotected carboxyl groups. Ring $Z^1$ is preferably a polycyclic alicyclic hydrocarbon ring (bridged hydrocarbon ring) such as adamantane ring.

Examples of substituted or unsubstituted alkyl groups having one to six carbon atoms as $R^2$, $R^3$, $R^4$, $R^6$, $R^7$ in Formula (8a), (8b), and (8d) include straight- or branched-chain alkyl groups each having one to six carbon atoms, such as methyl, ethyl, propyl, isopropyl, butyl, isobutyl, s-butyl, t-butyl, and hexyl groups; and haloalkyl groups each having one to six carbon atoms, such as trifluoromethyl group. In Formula (8c), alkyl groups as $R^5$ include, for example, straight- or branched-chain alkyl groups each having about one to about twenty carbon atoms, such as methyl, ethyl, propyl, isopropyl, butyl, isobutyl, s-butyl, t-butyl, hexyl, octyl, decyl, and dodecyl groups. Protected or unprotected hydroxyl groups as $R^5$ include, for example, hydroxyl group; and substituted oxy groups including alkoxy groups each having one to four carbon atoms, such as methoxy, ethoxy, and propoxy group. Protected or unprotected hydroxyalkyl groups include groups containing the protected or unprotected hydroxyl groups being combined through an alkylene group having one to six carbon atoms. Protected or unprotected carboxyl groups include —$COOR^d$ groups. In the formula, $R^d$ represents a hydrogen atom or an alkyl group. The alkyl group includes, for example, straight- or branched-chain alkyl groups each having one to six carbon atoms, such as methyl, ethyl, propyl, isopropyl, butyl, isobutyl, s-butyl, t-butyl, and hexyl groups. Tertiary hydrocarbon groups as $R^c$ of —$COOR^c$ group in $R^5$ include, for example, t-butyl, t-amyl, 2-methyl-2-adamantyl, and (1-methyl-1-adamantyl)ethyl groups. The tetrahydrofuranyl groups include 2-tetrahydrofuranyl group, the tetrahydropyranyl groups include 2-tetrahydropyranyl group, and the oxepanyl groups include 2-oxepanyl group.

Organic groups as $R^8$ include groups containing a hydrocarbon group and/or a heterocyclic group. Such hydrocarbon groups include aliphatic hydrocarbon groups, alicyclic hydrocarbon groups, aromatic hydrocarbon groups, and groups each containing two or more of these groups bound to each other. Aliphatic hydrocarbon groups include, for example, straight- or branched-chain alkyl groups, such as methyl, ethyl, propyl, isopropyl, butyl, isobutyl, s-butyl, t-butyl, hexyl, and octyl groups, of which alkyl groups each having one to eight carbon atoms are preferred; straight- or branched-chain alkenyl groups such as allyl group, of which alkenyl groups each having two to eight carbon atoms are preferred; straight- or branched-chain alkynyl groups such as propynyl group, of which alkynyl groups each having two to eight carbon atoms are preferred. Alicyclic hydrocarbon groups include, for example, cycloalkyl groups such as cyclopropyl, cyclopentyl, and cyclohexyl groups, of which cycloalkyl groups each having three to eight members are preferred; cycloalkenyl groups such as cyclopentenyl and cyclohexenyl groups, of which cycloalkenyl groups each having three to eight members are preferred; and bridged carbocyclic groups such as adamantyl and norbornyl groups, of which bridged carbocyclic groups each having four to twenty carbon atoms are preferred. Aromatic hydrocarbon groups include, for example, aromatic hydrocarbon groups having six to fourteen carbon atoms, such as phenyl and naphthyl groups. Groups each containing an aliphatic hydrocarbon group and an aromatic hydrocarbon group combined with each other include benzyl and 2-phenylethyl groups. These hydrocarbon groups may be substituted. Substituents herein include alkyl groups such as alkyl groups each having one to four carbon atoms; haloalkyl groups such as haloalkyl groups each having one to four carbon atoms; halogen atoms; protected or unprotected hydroxyl groups; protected or unprotected hydroxymethyl groups; protected or unprotected carboxyl groups; and oxo group. Protecting groups herein can be protecting groups generally used in organic syntheses.

The heterocyclic groups include heterocyclic groups containing at least one hetero atom selected from oxygen atom, sulfur atom, and nitrogen atom.

Preferred organic groups include alkyl groups each having one to eight carbon atoms, and organic groups each containing a cyclic skeleton. "Rings" for constituting the cyclic skeleton includes monocyclic or polycyclic, nonaromatic or aromatic carbocyclic rings or heterocyclic rings. Among them, monocyclic or polycyclic nonaromatic carbocyclic rings, and lactone rings to which a nonaromatic carbocyclic ring may be fused are preferred. Examples of monocyclic nonaromatic carbocyclic rings include cycloalkane rings each having about three to about fifteen members, such as cyclopentane ring and cyclohexane ring.

Examples of polycyclic nonaromatic carbocyclic rings (bridged carbocyclic rings) include adamantane ring; rings containing a norbornane ring or norbornene ring, such as norbornane ring, norbornene ring, bornane ring, isobornane ring, tricyclo[5.2.1.0$^{2,6}$]decane ring, and tetracyclo[4.4.0.1$^{2,5}$.1$^{7,10}$]dodecane ring; rings corresponding to polycyclic aromatic fused rings, except for being hydrogenated, such as perhydroindene ring, decalin ring (perhydronaphthalene ring), perhydrofluorene ring (tricyclo[7.4.0.0$^{3,8}$]tridecane ring), and perhydroanthracene ring, of which fully hydrogenated rings are preferred; and bridged carbocyclic rings each containing, for example, two, three, or four rings, such as tricyclo[4.2.2.1$^{2,5}$]undecane ring, of which bridged carbocyclic rings each having about six to about twenty carbon atoms are preferred. Lactone rings herein include, for example, gamma-butyrolactone ring, 4-oxatricyclo[4.3.1.1$^{3,8}$]undecan-5-one ring, 4-oxatricyclo[4.2.1.0$^{3,7}$]nonan-5-one ring, and 4-oxatricyclo[5.2.1.0$^{2,6}$]decan-5-one ring.

Rings for constituting the cyclic skeleton may be substituted. Such substituents include alkyl groups such as methyl group, of which alkyl groups each having one to four carbon atoms are preferred; haloalkyl groups such as trifluoromethyl groups, of which haloalkyl groups each having one to four carbon atoms are preferred; halogen atoms such as chlorine atom and fluorine atom; protected or unprotected hydroxyl groups; protected or unprotected hydroxyalkyl groups; protected or unprotected mercapto groups; protected or unprotected carboxyl groups; protected or unprotected amino groups; and protected or unprotected sulfonic groups. Protecting groups herein can be protecting groups generally used in organic syntheses.

A ring constituting the cyclic skeleton may be combined with an oxygen atom (oxygen atom at the adjacent position to $R^8$) in Formula (8d) directly, or indirectly through a linkage group. Such linkage groups include straight- or branched-chain alkylene groups such as methylene, methylmethylene, dimethylmethylene, ethylene, propylene, and trimethylene groups; carbonyl group; oxygen atom (ether bond; —O—); oxycarbonyl group (ester bond; —COO—); aminocarbonyl group (amide bond; —CONH—); and groups each containing two or more groups combined with each other.

At least two of $R^6$, $R^7$, and $R^8$ may be combined to form a ring with an adjacent atom. Examples of the ring include cycloalkane rings such as cyclopropane ring, cyclopentane ring, and cyclohexane ring; oxygen-containing rings such as tetrahydrofuran ring, tetrahydropyran ring, oxepane ring; and bridged rings.

There may be stereoisomers in compounds represented by Formulae (8a), (8b), (8c), and (8d). Each of such stereoisomers can be used alone or in combination.

Representative examples of compounds represented by Formula (8a) include, but are not limited to, 2-(meth)acryloyloxy-2-methyladamantanes, 1-hydroxy-2-(meth)acryloyloxy-2-methyladamantanes, 5-hydroxy-2-(meth)acryloyloxy-2-methyladamantanes, and 2-(meth)acryloyloxy-2-ethyladamantanes.

Representative examples of compounds represented by Formula (8b) include, but are not limited to, 1-(1-(meth)acryloyloxy-1-methylethyl)adamantanes, 1-hydroxy-3-(1-(meth)acryloyloxy-1-methylethyl)adamantanes, 1-(1-ethyl-1-(meth)acryloyloxypropyl)adamantanes, and 1-(1-(meth)acryloyloxy-1-methylpropyl)adamantanes.

Representative examples of compounds represented by Formula (8c) include, but are not limited to, 1-t-butoxycarbonyl-3-(meth)acryloyloxyadamantanes and 1-(2-tetrahydropyranyloxycarbonyl)-3-(meth)acryloyloxyadamantanes.

Representative examples of compounds represented by Formula (8d) include, but are not limited to, 1-adamantyloxy-1-ethyl(meth)acrylates, 1-adamantylmethyloxy-1-ethyl(meth)acrylates, 2-(1-adamantylethyl)oxy-1-ethyl (meth)acrylates, 1-bornyloxy-1-ethyl(meth)acrylates, 2-norbornyloxy-1-ethyl(meth)acrylates, 2-tetrahydropyranyl (meth)acrylates, and 2-tetrahydrofuranyl(meth)acrylates.

Each of compounds represented by Formula (8d) can be prepared by reacting a corresponding vinyl ether compound with (meth)acrylic acid according to a conventional procedure using an acid catalyst. For example, 1-adamantyloxy-1-ethyl(meth)acrylates can be prepared by reacting 1-adamantyl vinyl ether with (meth)acrylic acid in the presence of an acid catalyst.

Other examples of polymerizable unsaturated monomers corresponding to the other monomeric units include monomers that can impart or improve hydrophilicity and/or water-solubility. Such monomers include, for example, polar group-containing monomers such as hydroxyl-containing monomers including hydroxyl-protected compounds; mercapto-containing monomers including mercapto-protected compounds; carboxyl-containing monomers including carboxyl-protected compounds; amino-containing monomers including amino-protected compounds; sulfonic-containing monomers including sulfonic-protected compounds; lactone skeleton-containing monomers; cyclic ketone skeleton-containing monomers; acid anhydride-containing monomers; and imido-containing monomers.

Representative example of polar group-containing monomers include monomers represented by following Formula (9):

[Chemical Formula 14]

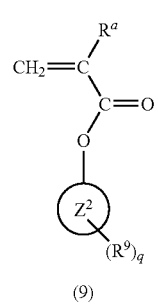

(9)

In Formula (9), Ring $Z^2$ represents an alicyclic hydrocarbon ring having six to twenty carbon atoms; $R^a$ is as defined above; $R^9$s are substituents bound to Ring $Z^2$, are the same as or different from one another, and each represent an oxo group, an alkyl group, a protected or unprotected hydroxyl group, a protected or unprotected hydroxyalkyl group, a protected or unprotected carboxyl group, a protected or unprotected amino group, or a protected or unprotected sulfonic group, where at least one of qR⁹s represents an oxo group, a protected or unprotected hydroxyl group, a protected or unprotected hydroxyalkyl group, a protected or unprotected carboxyl group, a protected or unprotected amino group, or a protected or unprotected sulfonic group; and "q" represents an integer of 1 to 3.

An alicyclic hydrocarbon ring having six to twenty carbon atoms as Ring $Z^2$ may be a monocyclic ring or a polycyclic ring such as a fused ring or a bridged ring. Representative examples of such alicyclic hydrocarbon rings include cyclohexane ring, cyclooctane ring, cyclodecane ring, adamantane ring, norbornane ring, norbornene ring, bornane ring, isobornane ring, perhydroindene ring, decalin ring, perhydrofluorene ring (tricyclo[7.4.0.0$^{3,8}$]tridecane ring), perhydroanthracene ring, tricyclo[5.2.1.0$^{2,6}$]decane ring, tricyclo [4.2.2.1$^{2,5}$]undecane ring, and tetracyclo[4.4.0.1$^{2,5}$.1$^{7,10}$] dodecane ring. These alicyclic hydrocarbon rings may be substituted. Such substituents include alkyl groups such as methyl group, of which alkyl groups each having one to four carbon atoms are preferred; haloalkyl groups such as trifluoromethyl group; halogen atoms such as fluorine atom and chlorine atom; protected or unprotected hydroxyl groups; protected or unprotected hydroxyalkyl groups; protected or unprotected mercapto groups; oxo group; protected or unprotected carboxyl groups; protected or unprotected amino groups; and protected or unprotected sulfonic groups.

Alkyl groups as $R^9$ in Formula (9) include straight- or branched-chain alkyl groups each having about one to about twenty carbon atoms, such as methyl, ethyl, propyl, isopropyl, butyl, isobutyl, s-butyl, t-butyl, hexyl, octyl, decyl, and dodecyl groups. Protected or unprotected amino groups include amino group; and substituted amino groups including alkylamino groups each having one to four carbon atoms, such as methylamino, ethylamino, and propylamino groups. Protected or unprotected sulfonic groups include a —SO$_3$R$^e$ group, in which $R^e$ represents a hydrogen atom or an alkyl group. The alkyl group includes straight- or branched-chain alkyl groups having one to six carbon atoms, such as methyl, ethyl, propyl, isopropyl, butyl, isobutyl, s-butyl, t-butyl, and hexyl groups. Protected or unprotected hydroxyl groups, protected or unprotected hydroxyalkyl groups, protected or unprotected mercapto groups, and protected or unprotected carboxyl groups as $R^9$ are as above.

Representative examples of compounds represented by Formula (9) include, but are not limited to, 1-hydroxy-3-(meth)acryloyloxyadamantanes, 1,3-dihydroxy-5-(meth)acryloyloxyadamantanes, 1-carboxy-3-(meth)acryloyloxyadamantanes, 1,3-dicarboxy-5-(meth)acryloyloxyadamantanes, 1-carboxy-3-hydroxy-5-(meth)acryloyloxyadamantanes, 1-t-butoxycarbonyl-3-(meth)acryloyloxyadamantanes, 1,3-bis(t-butoxycarbonyl)-5-(meth)acryloyloxyadamantanes, 1-t-butoxycarbonyl-3-hydroxy-5-(meth)acryloyloxyadamantanes, 1-(2-tetrahydropyranyloxycarbonyl)-3-(meth)acryloyloxyadamantanes, 1,3-bis(2-tetrahydropyranyloxycarbonyl)-5-(meth)acryloyloxyadamantanes, 1-hydroxy-3-(2-tetrahydropyranyloxycarbonyl)-5-(meth)acryloyloxyadamantanes, and 1-(meth)acryloyloxy-4-oxoadamantanes.

Other representative examples of polar group-containing monomers are lactone ring-containing monomers other than compounds represented by Formula (1). Specific examples of the lactone ring-containing monomers include, but are not limited to, 1-(meth)acryloyloxy-4-oxatricyclo[4.3.1.1$^{3,8}$]undecan-5-one, 1-(meth)acryloyloxy-4,7-dioxatricyclo [4.4.1.1$^{3,9}$]dodecane-5,8-dione, 1-(meth)acryloyloxy-4,8-dioxatricyclo[4.4.1.1$^{3,9}$]dodecane-5,7-dione, 1-(meth)acryloyloxy-5,7-dioxatricyclo[4.4.1.1$^{3,9}$]dodecane-4,8-dione, 2-(meth)acryloyloxy-4-oxatricyclo[4.2.1.0$^{3,7}$]nonan-5-one, 2-(meth)acryloyloxy-2-methyl-4-oxatricyclo [4.2.1.0$^{3,7}$]nonan-5-one, 2-(meth)acryloyloxy-6-methyl-4-oxatricyclo[4.2.1.0$^{3,7}$]nonan-5-one, 2-(meth)acryloyloxy-9-methyl-4-oxatricyclo[4.2.1.0$^{3,7}$]nonan-5-one, 2-(meth)acryloyloxy-9-carboxy-4-oxatricyclo[4.2.1.0$^{3,7}$]nonan-5-one, 2-(meth)acryloyloxy-9-methoxycarbonyl-4-oxatricyclo [4.2.1.0$^{3,7}$]nonan-5-one, 2-(meth)acryloyloxy-9-ethoxycarbonyl-4-oxatricyclo[4.2.1.0$^{3,7}$]nonan-5-one, 2-(meth)acryloyloxy-9-t-butoxycarbonyl-4-oxatricyclo [4.2.1.0$^{3,7}$]nonan-5-one, 8-(meth)acryloyloxy-4-oxatricyclo [5.2.1.0$^{2,6}$]decan-5-one, 9-(meth)acryloyloxy-4-oxatricyclo [5.2.1.0$^{2,6}$]decan-5-one, 4-(meth)acryloyloxy-6-oxabicyclo [3.2.1]octan-7-one, 4-(meth)acryloyloxy-4-methyl-6-oxabicyclo[3.2.1]octan-7-one, 4-(meth)acryloyloxy-5-methyl-6-oxabicyclo[3.2.1]octan-7-one, 4-(meth)acryloyloxy-4,5-dimethyl-6-oxabicyclo[3.2.1]octan-7-one, 6-(meth)acryloyloxy-2-oxabicyclo[2.2.2]octan-3-one, 6-(meth)acryloyloxy-6-methyl-2-oxabicyclo[2.2.2]octan-3-one, 6-(meth)acryloyloxy-1-methyl-2-oxabicyclo[2.2.2]octan-3-one, 6-(meth)acryloyloxy-1,6-dimethyl-2-oxabicyclo [2.2.2]octan-3-one, beta-(meth)acryloyloxy-gamma-butyrolactones, beta-(meth)acryloyloxy-alpha,alpha-dimethyl-gamma-butyrolactones, beta-(meth)acryloyloxy-gamma,gamma-dimethyl-gamma-butyrolactones, beta-(meth)acryloyloxy-alpha,alpha,beta-trimethyl-gamma-butyrolactones, beta-(meth)acryloyloxy-beta,gamma,gamma-trimethyl-gamma-butyrolactones, beta-(meth)acryloyloxy-alpha,alpha,beta,gamma,gamma-pentamethyl-gamma-butyrolactones, alpha-(meth)acryloyloxy-gamma-butyrolactones, alpha-(meth)acryloyloxy-alpha-methyl-gamma-butyrolactones, alpha-(meth)acryloyloxy-beta,beta-dimethyl-gamma-butyrolactones, alpha-(meth)acryloyloxy-alpha,beta,beta-trimethyl-gamma-butyrolactones, alpha-(meth)acryloyloxy-gamma,gamma-dimethyl-gamma-butyrolactones, alpha-(meth)acryloyloxy-alpha,gamma,gamma-trimethyl-gamma-butyrolactones, alpha-(meth)acryloyloxy-beta,beta,gamma,gamma-tetramethyl-gamma-butyrolactones, alpha-(meth)acryloyloxy-alpha,beta,beta,gamma,gamma-pentamethyl-gamma-butyrolactones, and gamma-(meth)acryloyloxy-gamma,gamma-dimethyl-gamma-butyrolactones.

Yet other examples of polar group-containing monomers include acrylic acid, methacrylic acid, maleic anhydride, and maleimide.

The content of monomeric units represented by Formula (I) in a polymeric compound according to the present invention is not specifically limited but is generally about 1 to about 100 percent by mole, preferably about 5 to about 80 percent by mole, and more preferably about 10 to about 60 percent by mole, of total monomeric units constituting the polymer. The content of monomeric units corresponding to monomers that can form carboxyl group as a result typically of a decomposition reaction is, for example, about 0 to about 95 percent by mole, preferably about 10 to about 90 percent by mole, and more preferably about 20 to about 60 percent by mole. The content of monomeric units corresponding to at least one monomer selected from hydroxyl-containing monomers, mercapto-containing monomers and carboxyl-containing monomers is, for example, about 0 to about 95 percent by mole, preferably about 5 to about 90 percent by mole, and more preferably about 10 to about 50 percent by mole.

Polymerization of a monomer mixture for the preparation of polymeric compounds according to the present invention can be carried out according to a conventional procedure for the preparation of, for example, acrylic polymers. Such procedures include solution polymerization, bulk polymerization, suspension polymerization, bulk-suspension polymerization, and emulsion polymerization. Among them, solution polymerization procedures are preferred, of which drop polymerization is more preferred. The drop polymerization may be carried out, for example, according to the following process (i), (ii), or (iii). In the process (i), a monomer solution in an organic solvent, and a polymerization initiator solution in an organic solvent are prepared respectively, and these solutions are added dropwise to an organic solvent held to a constant temperature, respectively. In the process (ii), a mixed solution containing a monomer and a polymerization initiator in an organic solvent is prepared and added dropwise to an organic solvent held to a constant temperature. In the process (iii), a monomer solution in an organic solvent, and a polymerization initiator solution in an organic solvent are prepared respectively, and the polymerization initiator solution is added dropwise to the monomer solution held to a constant temperature.

Known solvents can be used for polymerization. Examples of such solvents include ethers including chain ethers such as diethyl ether, and propylene glycol monomethyl ether and other glycol ethers, and cyclic ethers such as tetrahydrofuran and dioxane; esters including methyl acetate, ethyl acetate, butyl acetate, ethyl lactate, and glycol ether esters such as propylene glycol monomethyl ether acetate; ketones such as acetone, methyl ethyl ketone, methyl isobutyl ketone, and cyclohexanone; amides such as N,N-dimethylacetamide and N,N-dimethylformamide; sulfoxides such as dimethyl sulfoxide; alcohols such as methanol, ethanol, and propanol; hydrocarbons including aromatic hydrocarbons such as benzene, toluene, and xylenes, aliphatic hydrocarbons such as hexane, and alicyclic hydrocarbons such as cyclohexane; and mixtures of these solvents. Known polymerization initiators can be used herein. A polymerization temperature can be appropriately selected within the range of, for example, about 30° C. to about 150° C.

Polymers obtained as a result of polymerization can be purified by precipitation or reprecipitation. A solvent for use in precipitation or reprecipitation can be any of organic solvents and water, and it may be a solvent mixture. Organic solvents for use in precipitation or reprecipitation include, for example, hydrocarbons including aliphatic hydrocarbons such as pentane, hexane, heptane, and octane, alicyclic hydrocarbons such as cyclohexane and methylcyclohexane, and aromatic hydrocarbons such as benzene, toluene, and xylenes; halogenated hydrocarbons including halogenated aliphatic hydrocarbons such as methylene chloride, chloroform, and carbon tetrachloride, and halogenated aromatic hydrocarbons such as chlorobenzene and dichlorobenzene; nitro compounds such as nitromethane and nitroethane; nitriles such as acetonitrile and benzonitrile; ethers including chain ethers such as diethyl ether, diisopropyl ether, and dimethoxyethane, and cyclic ethers such as tetrahydrofuran and dioxane; ketones such as acetone, methyl ethyl ketone, and diisobutyl ketone; esters such as ethyl acetate and butyl acetate; carbonates such as dimethyl carbonate, diethyl carbonate, ethylene carbonate, and propylene carbonate; alcohols such as methanol, ethanol, propanol, isopropyl alcohol, and butanol; carboxylic acids such as acetic acid; and solvent mixtures containing these solvents.

Among them, solvents containing at least a hydrocarbon are preferred as organic solvents for use in the precipitation or reprecipitation. Such solvents more preferably contain an aliphatic hydrocarbon such as hexane. The ratio of a hydrocarbon (e.g., an aliphatic hydrocarbon such as hexane) to another solvent in the solvent containing at least a hydrocarbon is, for example, about 10/90 to about 99/1, preferably about 30/70 to about 98/2, and more preferably about 50/50 to about 97/3, in terms of volume ratio at 25° C.

Polymeric compounds may each have a weight-average molecular weight (Mw) of, for example, about 1000 to about 500000, and preferably about 3000 to about 50000, and a molecular weight distribution (Mw/Mn) of, for example, about 1.5 to about 2.5. The symbol "Mn" indicates a number-average molecular weight, and Mn and Mw are molecular weights in terms of polystyrene.

Polymeric compounds according to the present invention are highly stable to, for example, chemicals, are excellently soluble in an organic solvent, are highly hydrolyzable, and hydrolyzed products thereof are highly soluble in water. Accordingly, they can be used as highly functional polymers in a variety of fields.

EXAMPLES

The present invention will be illustrated in further detail with reference to several examples below, which by no means limit the scope of the present invention. The symbol "Et" in chemical formulae represents ethyl group. The weight-average molecular weight (Mw) and the number-average molecular weight (Mn) of a sample polymer are values in terms of standard polystyrene as determined by gel permeation chromatographic (GPC) analysis using a refractive index system (RI). The gel permeation chromatography was carried out using three columns "KF-806L" (Showa Denko K.K.) connected in series under conditions of a column temperature of 40° C., an RI temperature of 40° C., and tetrahydrofuran flow rate of 0.8 ml/min.

Example 1

According to the following reaction process formula, 5-methacryloyloxy-3-oxatricyclo[4.2.1.0$^{4,8}$]nonan-2-one was prepared.

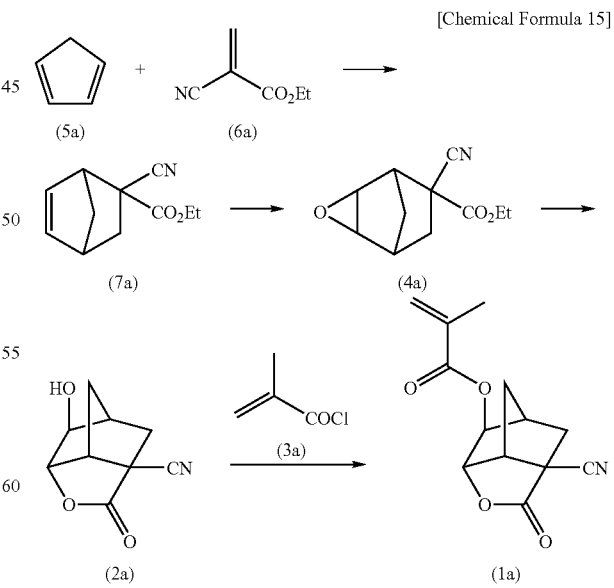

[Chemical Formula 15]

Specifically, 50 g (0.33 mol) of ethyl 2-cyanoacrylate (6a) was dissolved in 200 ml of toluene, and 45 g (0.68 mol) of 1,3-cyclopentadiene (5a) was added dropwise to the solution with cooling temperatures of 35° C. or below. Stirring for one hour and subsequent enrichment yielded 72 g of ethyl 5-cyanobicyclo[2.2.1]hept-2-ene-5-carboxylate represented by Formula (7a) (crude product).

The above-prepared compound represented by Formula (7a) (crude product) (69 g; in terms of 0.36 mol) was dissolved in 501 g of methylene chloride, and 115 g of m-chloroperbenzoic acid (m-CPBA) was gradually added to the solution with cooling to 5° C. or below. Four hours later, excess peroxide was decomposed by the addition of an aqueous sodium sulfite solution, and the organic layer was washed with an aqueous sodium hydrogen carbonate solution. To the organic layer containing a compound represented by Formula (4a) were added 150 g of formic acid and 303 g of water, the mixture was raised in temperature to 50° C. and was stirred for further four hours. The aqueous layer was extracted with ethyl acetate until no product was detected. Organic layers were combined and concentrated, and thereby yielded 23 g of 1-cyano-5-hydroxy-3-oxatricyclo[4.2.1.0$^{4,8}$]nonan-2-one represented by Formula (2a) (crude product).

Spectral data of 1-cyano-5-hydroxy-3-oxatricyclo [4.2.1.0$^{4,8}$]nonan-2-one represented by Formula (2a)

$^1$H-NMR (CDCl$_3$) δ: 4.52-4.54 (1H), 3.69-3.73 (2H), 2.54-2.55 (1H), 2.29-2.35 (2H), 2.13-2.16 (1H), 1.85-1.88 (1H)

In 252 g of tetrahydrofuran (THF) was dissolved 23 g (in terms of 0.127 mol) of the above-prepared compound represented by Formula (2a) (crude product). The solution was combined with 16.9 g of triethylamine and 0.2 g of hydroquinone and was further combined with 18.3 g of methacryloyl chloride (3a) added dropwise while cooling the mixture to 5° C. The reaction mixture was combined with 300 ml of water and was extracted with ethyl acetate. The organic layer was sequentially washed with an aqueous sodium hydrogen carbonate solution and water, was concentrated, the concentrate was crystallized from diisopropyl ether and thereby yielded 14 g of 1-cyano-5-methacryloyloxy-3-oxatricyclo [4.2.1.0$^{4,8}$]nonan-2-one represented by Formula (1a).

Spectral data of 1-cyano-5-methacryloyloxy-3-oxatricyclo[4.2.1.0$^{4,8}$]nonan-2-one represented by Formula (1a)

$^1$H-NMR (CDCl$_3$) δ: 6.12 (d, 1H), 5.69 (d, 1H), 4.83 (1H), 4.69 (1H), 3.82-3.83 (1H), 2.78 (1H), 2.27-2.45 (3H), 2.04 (1H), 1.93 (3H)

Example 2

Synthesis of polymeric compound having following structure:

[Chemical Formula 16]

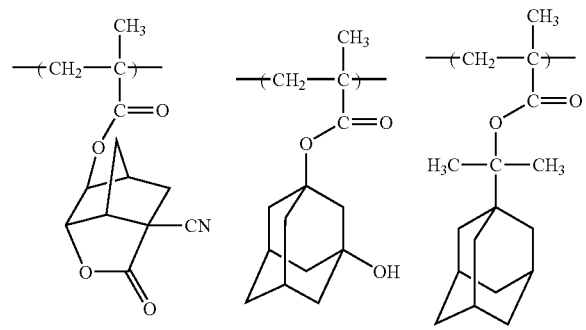

In a round-bottom flask having a reflux condenser, a stirrer, and a T-shape stopcock were placed 35.7 g of propylene glycol monomethyl ether acetate (PGMEA) and 23.8 g of propylene glycol monomethyl ether (PGME) under nitrogen atmosphere. To the stirred solution held at a temperature of 100° C. was added dropwise a monomer solution at a constant rate over six hours. The monomer solution contained 11.82 g (47.8 mmol) of 1-cyano-5-methacryloyloxy-3-oxatricyclo [4.2.1.0$^{4,8}$]nonan-2-one, 5.65 g (23.9 mmol) of 1-hydroxy-3-methacryloyloxyadamantane, 12.54 g (47.8 mmol) of 1-(1-methacryloyloxy-1-methylethyl)adamantane, 0.75 g of dimethyl 2,2'-azobisisobutylate [the product of Wako Pure Chemical Industries, Ltd. under the trade name of "V-601"], 66.3 g of PGMEA, and 44.2 g of PGME. After the completion of dropwise addition, the mixture was stirred for further two hours. After the completion of polymerization reaction, the resulting reaction mixture was filtrated through a filter with a pore size of 0.1 μm and was added dropwise to a stirred 9:1 mixture (by volume; 25° C.) of hexane and ethyl acetate in an amount as much as 7 times the reaction mixture. The precipitates were separated by filtration and thereby yielded 24.0 g of the target resin. The recovered polymer was analyzed by GPC and was found to have a weight-average molecular weight (Mw) of 8100 and a molecular weight distribution (Mw/Mn) of 1.91.

Example 3

Synthesis of polymeric compound having following structure:

[Chemical Formula 17]

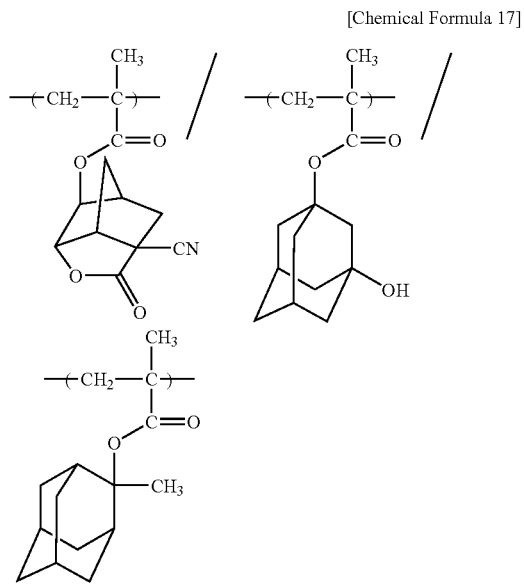

The target resin (21.9 g) was prepared by the procedure of Example 1, except for using, as monomeric components, 12.37 g (50.1 mmol) of 1-cyano-5-methacryloyloxy-3-oxatricyclo[4.2.1.0$^{4,8}$]nonan-2-one, 5.91 g (25.0 mmol) of 1-hydroxy-3-methacryloyloxyadamantane, and 11.72 g (50.1 mmol) of 2-methacryloyloxy-2-methyladamantane. The recovered polymer was analyzed by GPC and was found to have a weight-average molecular weight (Mw) of 9100 and a molecular weight distribution (Mw/Mn) of 1.96.

Example 4

Synthesis of polymeric compound having following structure:

[Chemical Formula 18]

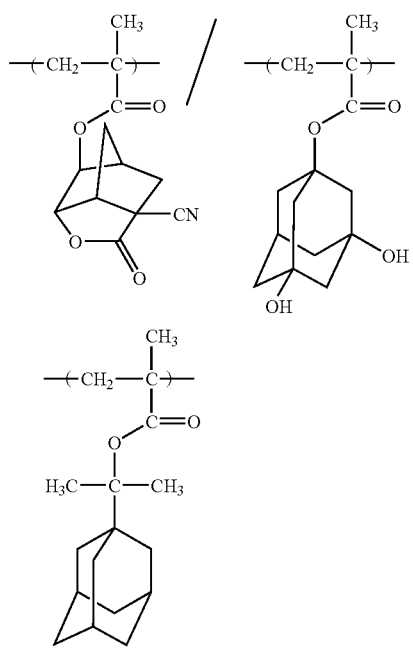 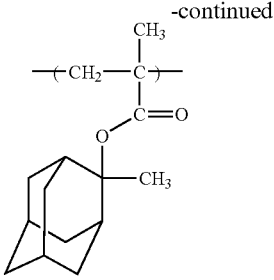

The target resin (22.8 g) was prepared by the procedure of Example 1, except for using, as monomeric components, 11.67 g (47.2 mmol) of 1-cyano-5-methacryloyloxy-3-oxatricyclo[4.2.1.0$^{4,8}$]nonan-2-one, 5.95 g (23.6 mmol) of 1,3-dihydroxy-5-methacryloyloxyadamantane, and 12.38 g (47.2 mmol) of 1-(1-methacryloyloxy-1-methylethyl)adamantane. The recovered polymer was analyzed by GPC and was found to have a weight-average molecular weight (Mw) of 7800 and a molecular weight distribution (Mw/Mn) of 1.90.

Example 5

Synthesis of polymeric compound having following structure:

[Chemical Formula 19]

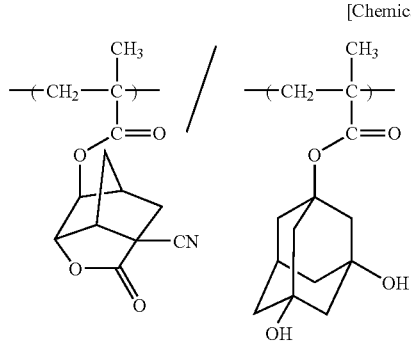

The target resin (21.0 g) was prepared by the procedure of Example 1, except for using, as monomeric components, 12.21 g (49.4 mmol) of 1-cyano-5-methacryloyloxy-3-oxatricyclo[4.2.1.0$^{4,8}$]nonan-2-one, 6.23 g (24.7 mmol) of 1,3-dihydroxy-5-methacryloyloxyadamantane, and 11.57 g (49.4 mmol) of 2-methacryloyloxy-2-methyladamantane. The recovered polymer was analyzed by GPC and was found to have a weight-average molecular weight (Mw) of 8700 and a molecular weight distribution (Mw/Mn) of 1.95.

Evaluation Test

Each one gram of the respective resins prepared according to Examples 2 to 5 was mixed with 9 g of a 6:4 (by weight) solvent mixture of propylene glycol monomethyl ether acetate (PGMEA) and propylene glycol monomethyl ether (PGME) and was stirred at room temperature. As a result, the resins were smoothly dissolved and yielded homogenous solutions.

The invention claimed is:

1. A polycyclic alcohol comprising a cyano group and a lactone skeleton, represented by following Formula (2):

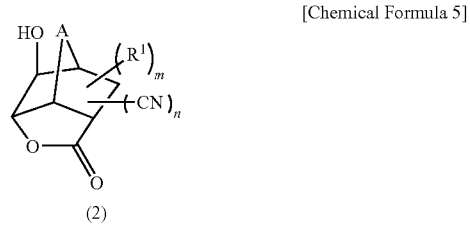

[Chemical Formula 5]

(2)

wherein $R^1$s are substituents bound to a ring and each represent a halogen atom, an alkyl group having one to six carbon atoms which may have a halogen atom, a hydroxyalkyl group having one to six carbon atoms whose hydroxyl moiety may be protected by a protecting group and which may have a halogen atom, a carboxyl group which may form a salt, or a substituted oxycarbonyl group; "A" represents nonbonding or a methylene group; "m" is the number of $R^1$s and represents an integer of 0 to 8; "n" is the number of cyano groups (CN) bound to the ring and represents an integer of 1 to 9; and "OH" may have either of an endo conformation and an exo conformation.

2. A process for producing a polycyclic alcohol containing a cyano group and a lactone skeleton as defined in claim 1, the process comprising the step of:

subjecting an epoxy compound to a cyclization reaction to thereby yield a polycyclic alcohol, the epoxy compound being represented by following Formula (4):

[Chemical Formula 6]

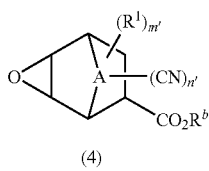

(4)

wherein $R^b$ represents an organic group; $R^1$s are substituents bound to a ring and each represent a halogen atom, an alkyl group having one to six carbon atoms which may have a halogen atom, a hydroxyalkyl group having one to six carbon atoms whose hydroxyl moiety may be protected by a protecting group and which may have a halogen atom, a carboxyl group which may form a salt, or a substituted oxycarbonyl group; "A" represents nonbonding or a methylene group; "m'" is the number of $R^1$s and represents an integer of 0 to 8; and "n'" is the number of cyano groups (CN) bound to the ring and represents an integer of 1 to 9, and the polycyclic alcohol being represented by following Formula (2):

[Chemical Formula 7]

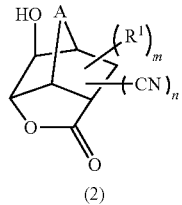

(2)

wherein $R^1$s are substituents bound to a ring and each represent a halogen atom, an alkyl group having one to six carbon atoms which may have a halogen atom, a hydroxyalkyl group having one to six carbon atoms whose hydroxyl moiety may be protected by a protecting group and which may have a halogen atom, a carboxyl group which may form a salt, or a substituted oxycarbonyl group; "A" represents nonbonding or a methylene group; "m" is the number of $R^1$s and represents an integer of 0 to 8; "n" is the number of cyano groups (CN) bound to the ring and represents an integer of 1 to 9; and "OH" may have either of an endo conformation and an exo conformation.

\* \* \* \* \*